United States Patent
Keller et al.

(10) Patent No.: US 8,211,180 B2
(45) Date of Patent: Jul. 3, 2012

(54) TEMPOROMANDIBULAR JOINT FOSSA-EMINENCE PROSTHESIS

(75) Inventors: Eugene E. Keller, Rochester, MN (US); Evre Baltali, Rochester, MN (US); Kai-Nan An, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 79 days.

(21) Appl. No.: 12/373,620

(22) PCT Filed: Jul. 19, 2007

(86) PCT No.: PCT/US2007/016368
§ 371 (c)(1),
(2), (4) Date: Nov. 10, 2009

(87) PCT Pub. No.: WO2008/011099
PCT Pub. Date: Jan. 24, 2008

(65) Prior Publication Data
US 2010/0057209 A1    Mar. 4, 2010

Related U.S. Application Data

(60) Provisional application No. 60/831,867, filed on Jul. 19, 2006.

(51) Int. Cl.
*A61F 2/02* (2006.01)

(52) U.S. Cl. .................................................. 623/17.17
(58) Field of Classification Search .... 623/17.17–17.19, 623/18.11, 19.11–19.14, 16.11, 14.12, 11.11, 623/21.11, 21.12
See application file for complete search history.

(56) References Cited

U.S. PATENT DOCUMENTS

| | | | |
|---|---|---|---|
| 3,178,728 A | 4/1965 | Christensen | |
| 3,488,779 A | 1/1970 | Christensen | |
| 3,579,643 A | 5/1971 | Morgan | |
| 4,917,701 A | 4/1990 | Morgan | |
| 4,919,668 A | 4/1990 | Rosenbaum et al. | |
| 4,936,852 A * | 6/1990 | Kent et al. | 623/17.17 |
| 5,405,393 A | 4/1995 | Falkenstrom | |
| 5,445,650 A | 8/1995 | Nealis | |
| 5,549,680 A * | 8/1996 | Gordon | 623/17.17 |
| 5,769,891 A | 6/1998 | Clayton | |
| 5,989,292 A | 11/1999 | Van Loon | |
| 6,132,466 A | 10/2000 | Holffman et al. | |

OTHER PUBLICATIONS

International Search Report and Written Opinion issued in PCT/US2007/016368, mailed Apr. 17, 2008, 9 pages.

* cited by examiner

*Primary Examiner* — Alvin J Stewart
(74) *Attorney, Agent, or Firm* — Faegre Baker Daniels LLP

(57) ABSTRACT

A fossa-eminence prosthesis having a nonanatomic surface that is relatively flatter than the native fossa. The articular eminence of the patient can be surgically reduced before implanting the prosthesis.

6 Claims, 22 Drawing Sheets

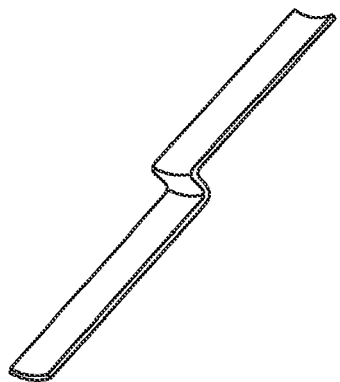
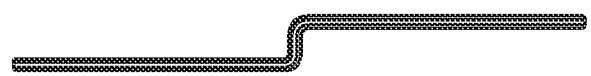
Fig. 17A
Fig. 17B
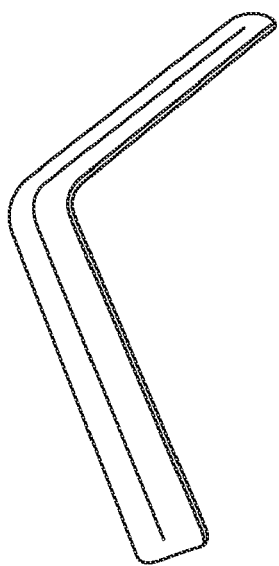
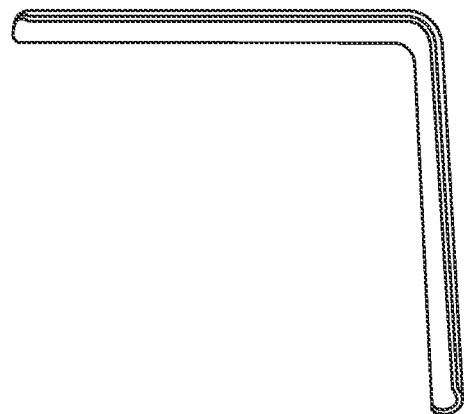
Fig. 17C
Fig. 17D

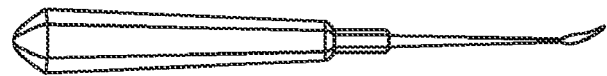
Fig. 19B
Fig. 19A
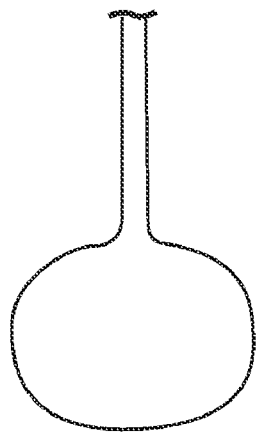
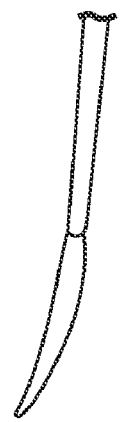
Fig. 20A
Fig. 20B

US 8,211,180 B2

TEMPOROMANDIBULAR JOINT FOSSA-EMINENCE PROSTHESIS

FIELD OF THE INVENTION

The invention is a fossa-eminence prosthesis for a temporomandibular joint.

BACKGROUND OF THE INVENTION

Metal fossa-eminence prostheses (hemijoint replacements) are generally known and commercially available. These devices are materials that are rigidly fixed to the articular fossa and/or materials that resurface the articular fossa to reverse bone-on-bone contact in patients with osteoarthritis or fibrous/osseous ankylosis. There remains a continuing need to improve fossa-eminence type prostheses. Prostheses that enhance joint motion are desirable. Improved instruments for use with eminence fossa implant surgical procedures involving fossa-eminence prostheses would also be desirable.

SUMMARY OF THE INVENTION

An improved fossa-eminence prosthesis in accordance with one embodiment of the invention has a nonanatomic surface that is relatively flatter than the native (healthy or diseased) articular fossa. In another embodiment of the invention the mid-part of the prosthesis is thicker than other parts to provide the relatively flatter surface. The articular eminence of the patient can be reduced before implanting the prosthesis.

BRIEF DESCRIPTION OF THE DRAWINGS

FIGS. 17A-17D are views of a second retractor in accordance with another embodiment of the invention that can be used to surgically implant the prosthesis shown in FIG. 2.

FIGS. 19A and 19B are plan and side views, respectively, of a scraper in accordance with another embodiment of the invention that can be used to surgically implant the prosthesis shown in FIG. 2.

FIGS. 20A and 20B are detailed plan and side views, respectively, of the working end of the scraper shown in FIGS. 19A and 19B.

FIG. 25A is a side view from the anterior side (looking anterior to posterior); FIG. 25B is a plan view of the surface engaged by the mandibular condyle (i.e., in a direction from the bottom of the skull); FIG. 25C is an end view from the lateral side (looking lateral to medial); and FIG. 25D is an isometric view showing the surface engaged by the mandibular condyle. Locations for four screw holes on the lateral side are shown by dots.

DETAILED DESCRIPTION OF THE INVENTION

The present invention is an implant surgically placed in the temporomandibular joint fossa/eminence (temporal bone) anatomy. The implant has a relatively flat nonanatomic surface that is surgically fit following osseous recontouring of TMJ fossa-eminence anatomy. It can be stabilized by endosseous screws.

Figure 1:
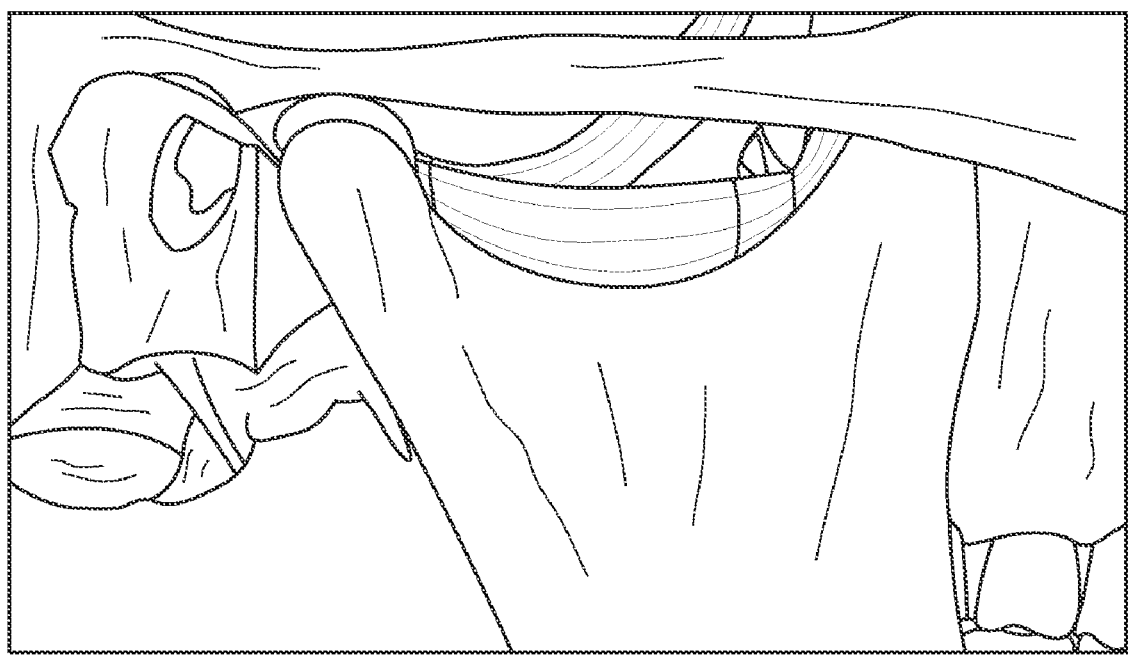
FIG. 1 is a right side view of a portion of a human skull illustrating an articular normal non-pathologic temporomandibular joint including a healthy articular disc between the mandible fossa of the temporal bone and the condylar process of the mandible.
Figure 2:
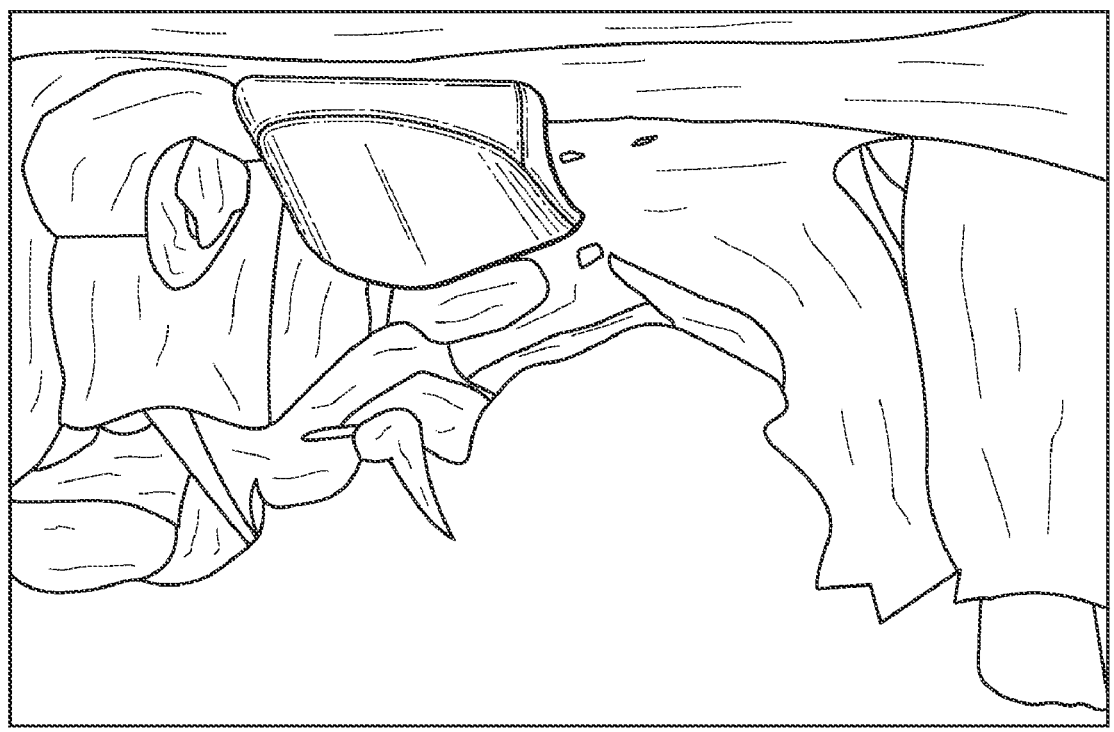
FIG. 2 is a right side view of a portion of a human skull, without the mandible, having a prosthesis in accordance with one embodiment of the present invention.
Figure 3:
FIG. 3 is a right side view of the skull and prosthesis shown in FIG. 2, with the mandible and its condyle engaged with the fossa of the prosthesis.
Figure 4:
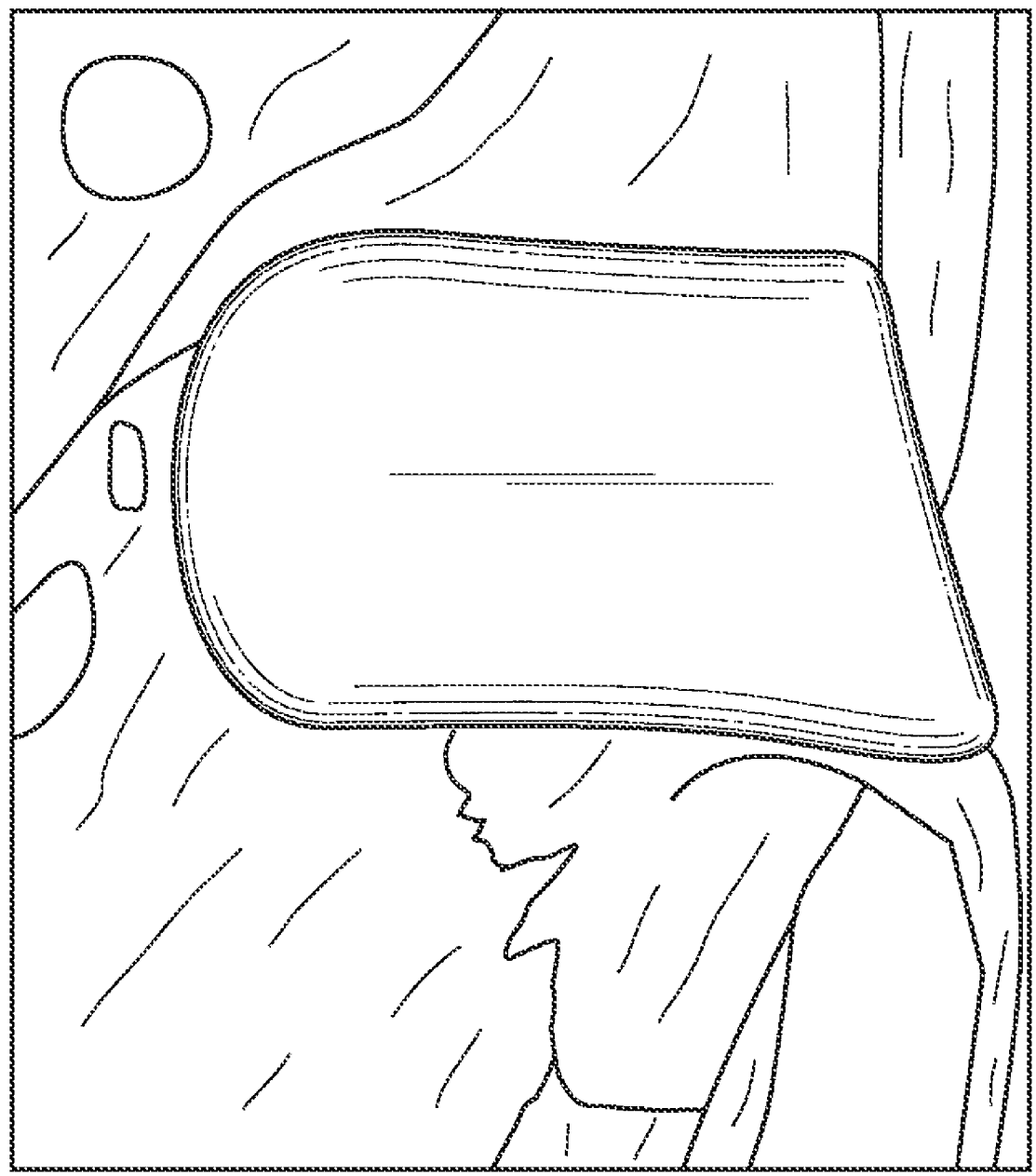
FIG. 4 is a view of the skull and prosthesis shown in FIG. 2, showing the fossa of the prosthesis from below the skull.
Figure 5:
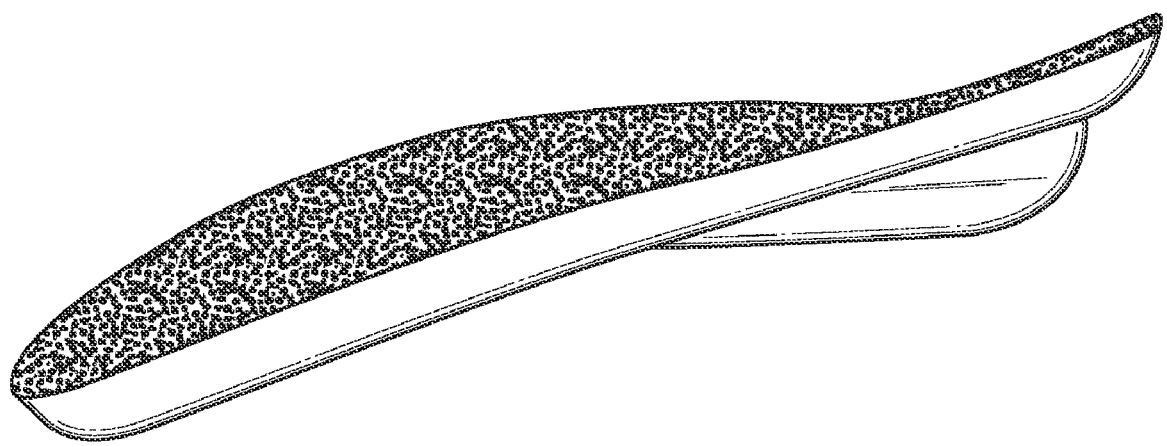
FIG. 5 is a back view of the prosthesis shown in FIG. 2.
Figure 6:
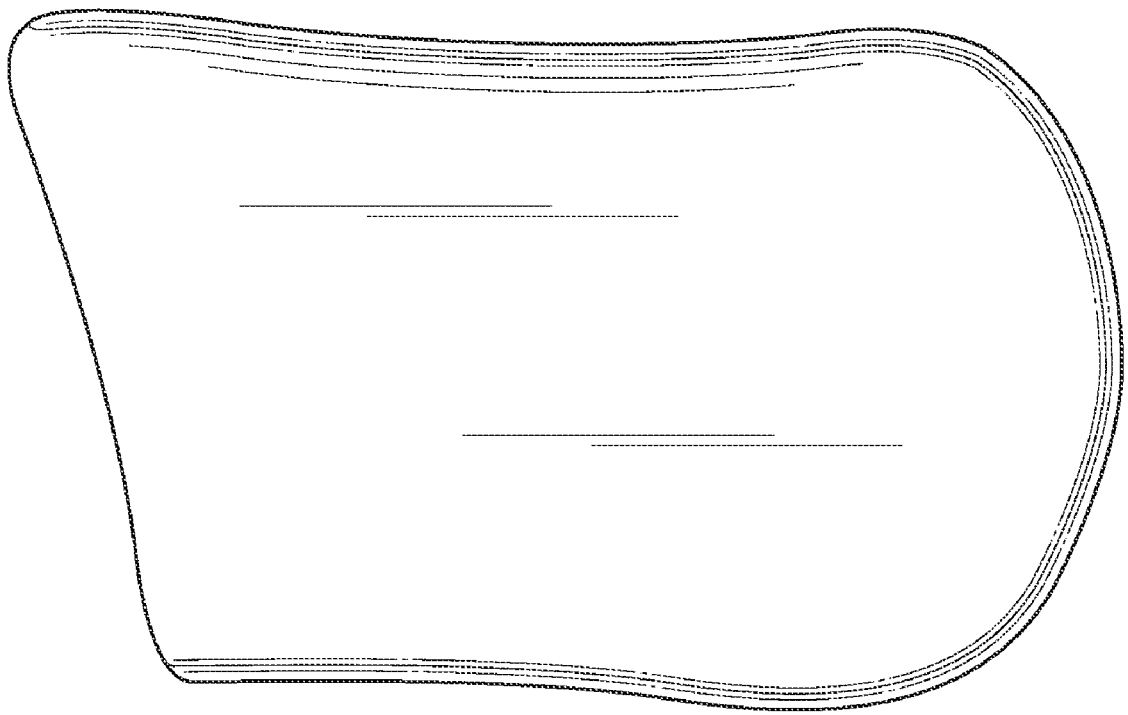
FIG. 6 is a bottom view of the prosthesis shown in FIG. 2.
Figure 7:
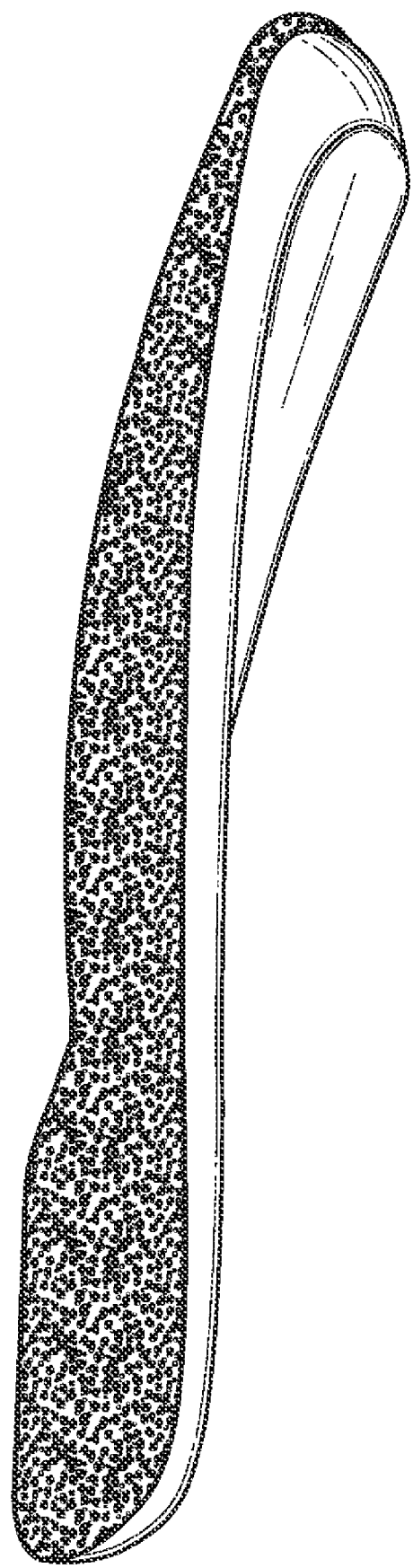
FIG. 7 is a front view of the prosthesis shown in FIG. 2.
Figure 8:
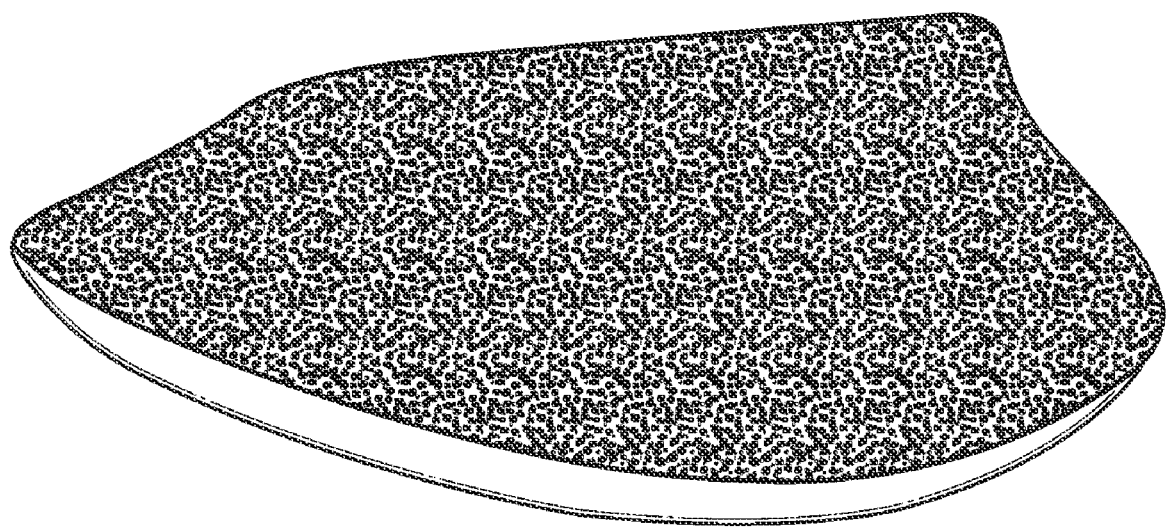
FIG. 8 is an interior view of the prosthesis shown in FIG. 2.
Figure 9:
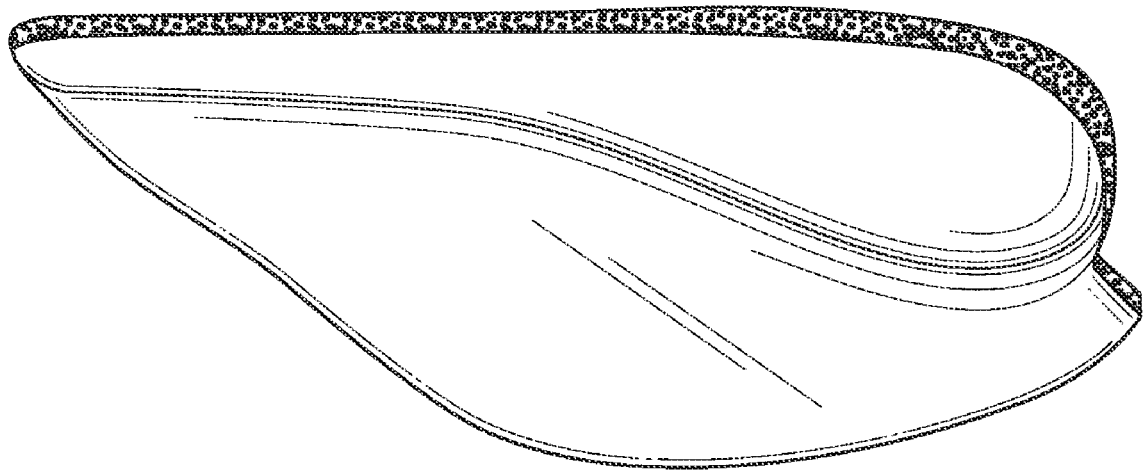
FIG. 9 is a side view of the prosthesis shown in FIG. 2.
Figure 10:
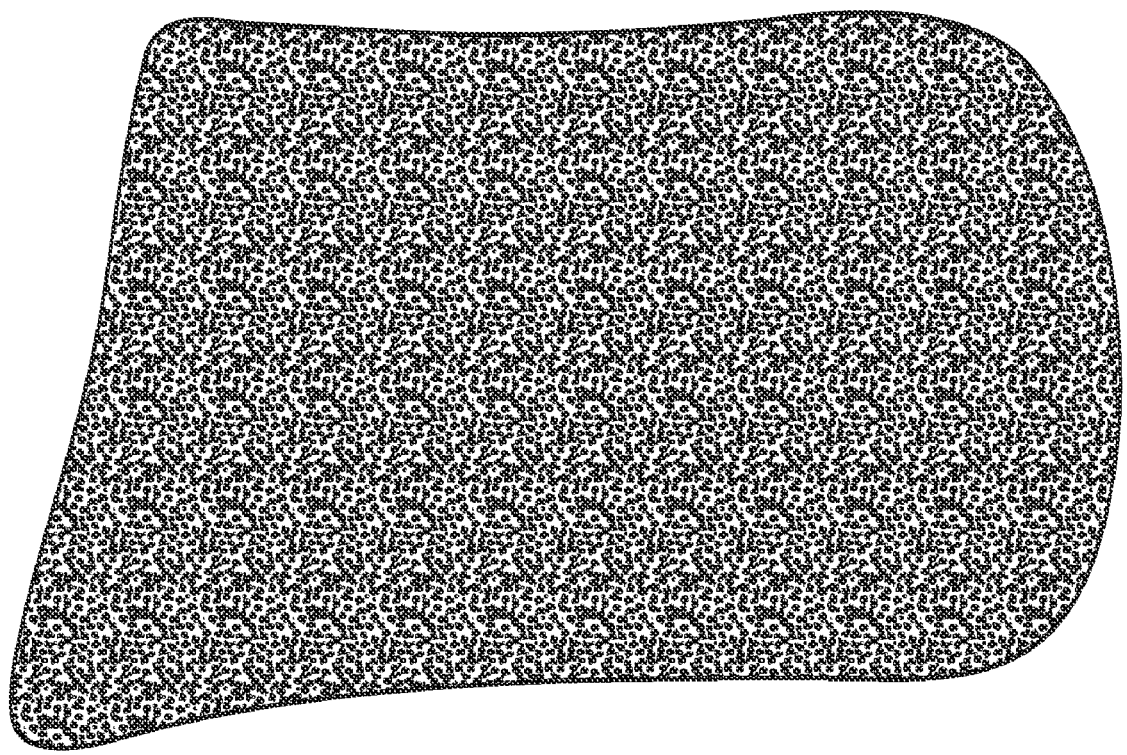
FIG. 10 is a top view of the prosthesis shown in FIG. 2.
Figure 11:
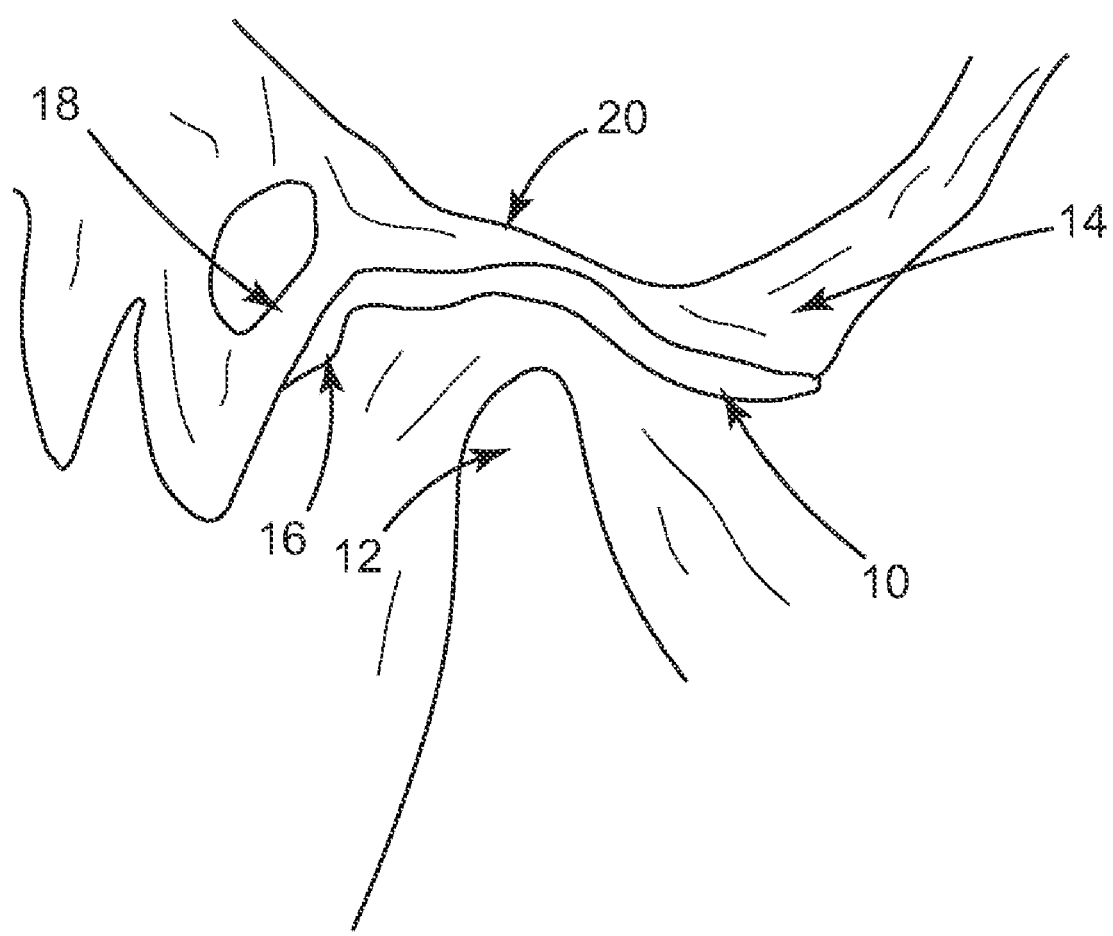
FIG. 11 is a sagittal view of a portion of a temporomandibular joint having a prosthesis 10 in accordance with another embodiment of the present invention. Prosthesis 10 has an overall relatively flat contour design to ease the movement of the mandibular condyle 12 and reduce the obstructive effect of articular eminence 14. The eminence was reduced during the surgical procedure. The mandibular condyle 12 can be smoothed during the surgical procedure. The mid region of the prosthesis 10 over the glenoid (articular) fossa 20 is thicker in other surrounding regions to provide the relatively flat surface of the design.
Figure 12:
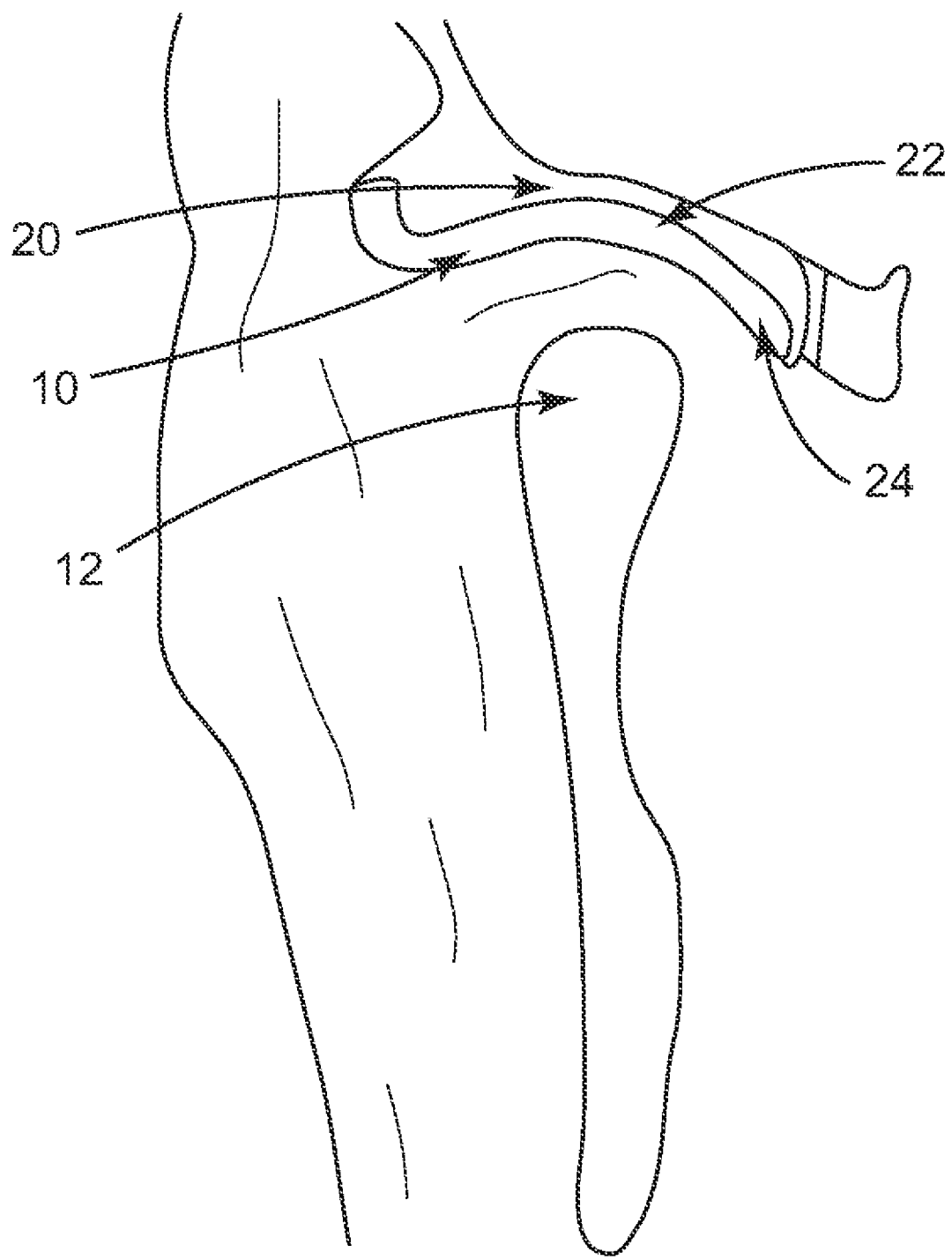
FIG. 12 is a coronal view of a portion of a temporomandibular joint and prosthesis 10 shown in FIG. 11. The mid region 22 of the prosthesis 10 is thicker than the other regions to provide the relatively flat contoured shape. The region 24 of the prosthesis 10 over the medial part of the glenoid fossa 20 has a slight curvature.
Figure 13:
FIG. 13 is a view of a portion of a human skull showing the anatomy of the natural temporal (articular) fossa (i.e., before surgery in accordance with one embodiment of the invention.
Figure 14:
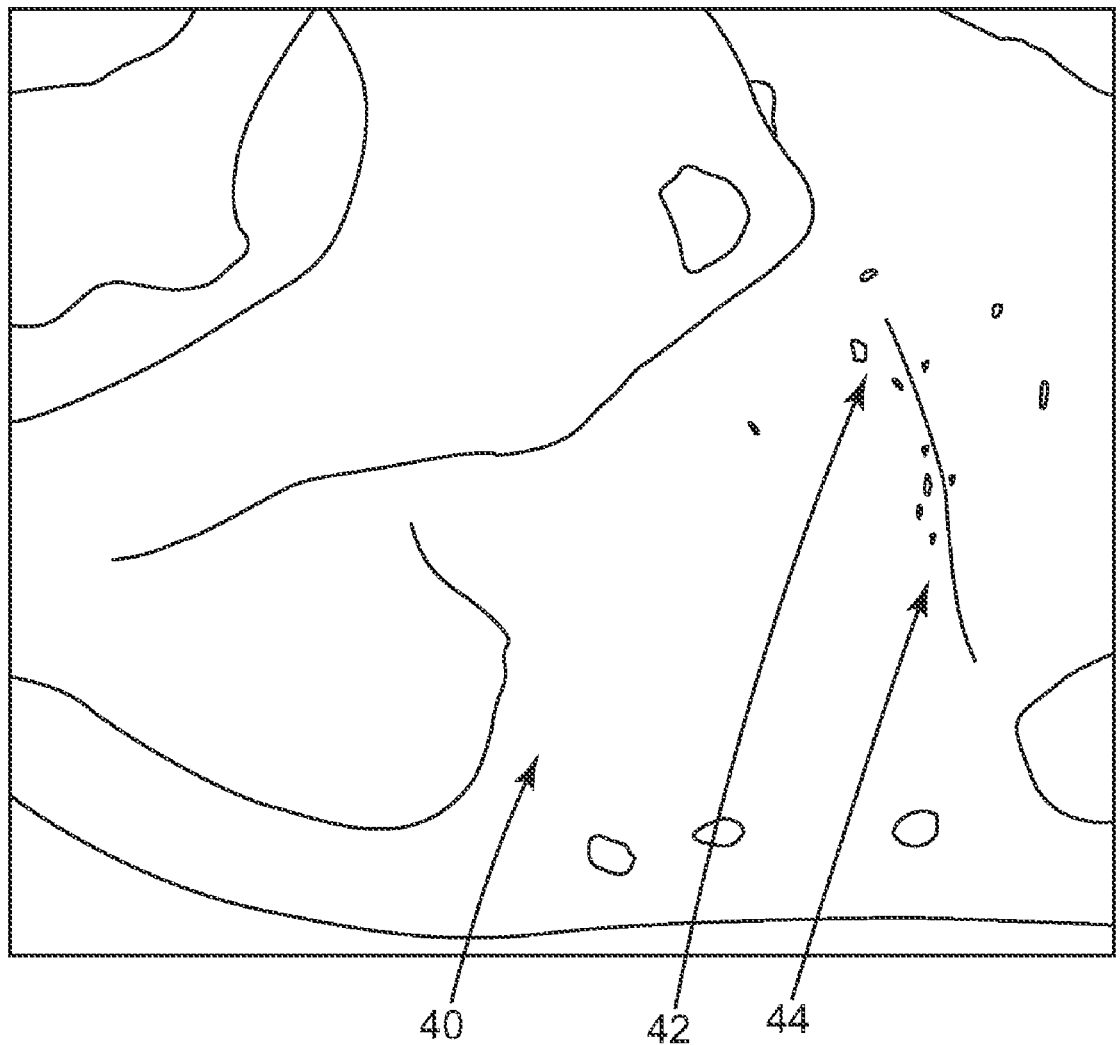
FIG. 14 is a view of the portion of the skull shown in FIG. 13 following surgical reduction of the articular eminence and recontouring of the glenoid fossa.
Figure 15:
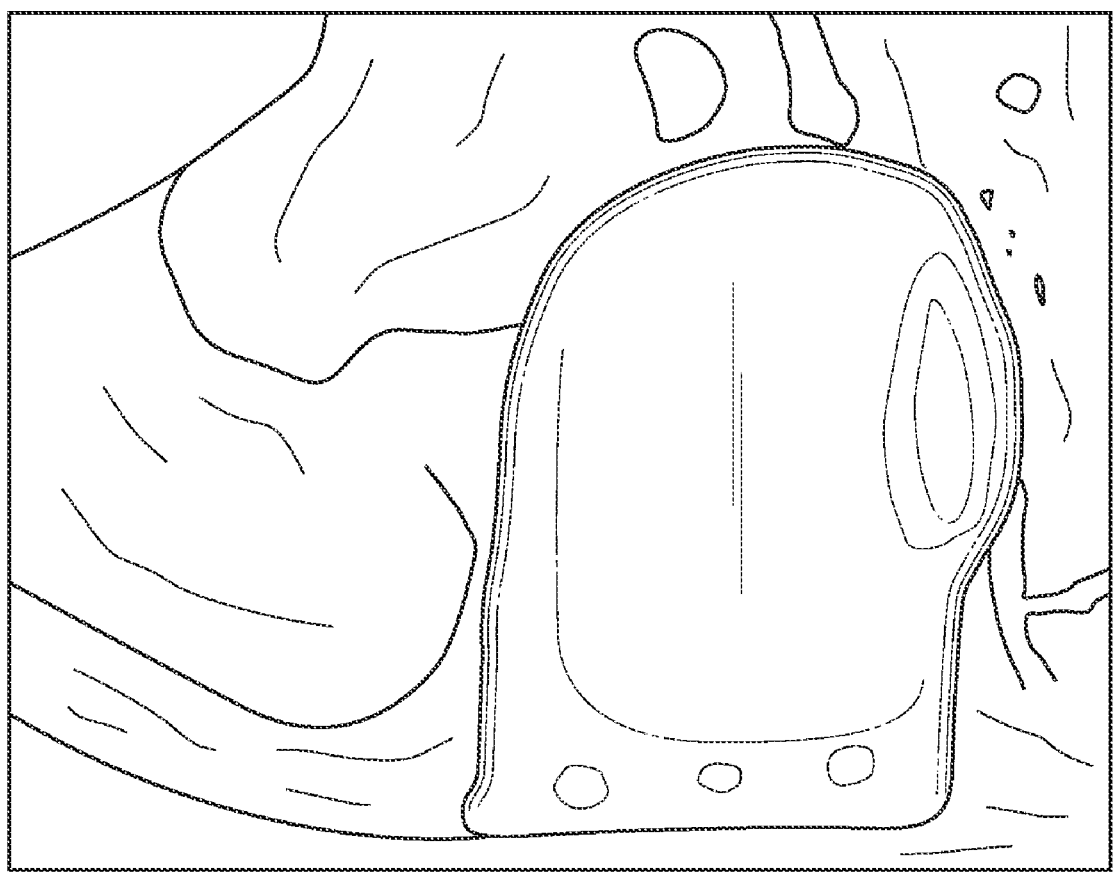
FIG. 15 is a view of the portion of the skull shown in FIG. 14 with an implanted prosthesis in accordance with the present invention.

FIGS. 2-15 and 25A-25D illustrate several embodiments of metal fossa-eminence prostheses (hemijoints) in accordance with the present invention. The prostheses differs from the duplication of healthy human fossa-eminence anatomy (e.g., that shown in FIG. 1) in that they are generally flatter and have broader temporal surface coverage. These characteristics of the device are achieved at least in part by reducing portions of the articular eminence prior to implantation, and making the mid-part of the device thicker than other parts. The base of the valley in the mid-part is therefore higher than in an anatomical duplicate. The illustrated fixation endosseous screws are also improved to be more effective and user friendly. The flat design reduces the obstructing anatomy of the articular eminence to provide enhanced condyle motion. Use of the prosthesis in connection with eminoplasty and condyloplasty allow for favorable joint healing and biomechanics.

Figure 16A:
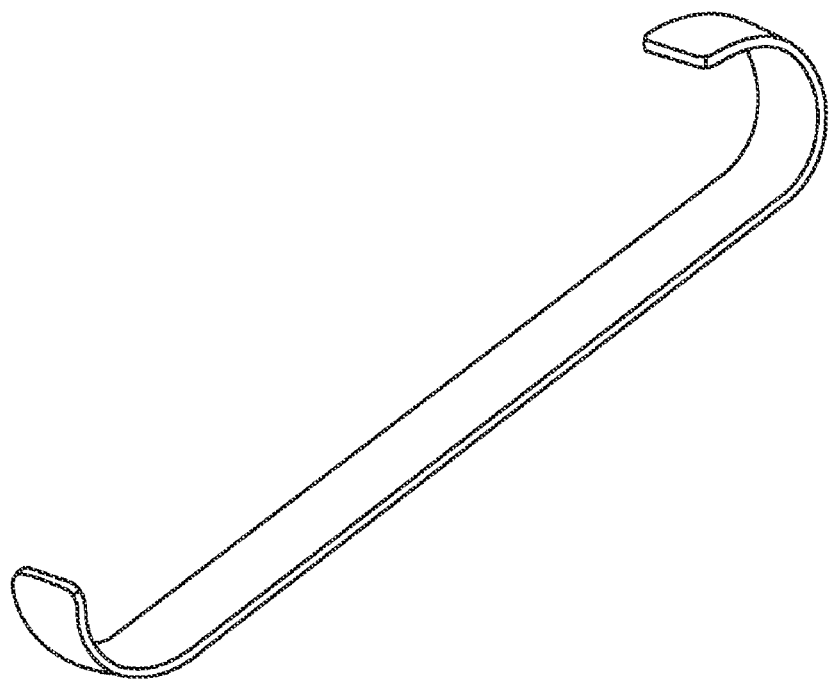
FIGS. 16A and 16B are isometric and side views, respectively, of a first retractor in accordance with one embodiment of the invention that can be used to surgically implant the prosthesis shown in FIG. 2.
Figure 16B:

The retractor shown in FIGS. 16A and 16B can be used for tissue retraction. The retractor has an approximately 180° circular loop or hook on one and an approximately 135° circular loop or hook on the other end. This retractor can be used to retract the tissue after preauricular flap development. Different ends can be alternated to fit the thickness and depth of tissue to be retracted.

The retractor shown in FIGS. 17A-17D can be used for protecting and retracting the condyle away from the fossa during fossa-eminence debridement and recontouring. One end is wider than the other end. The wide end fits on the deep medial part of the fossa and keeps the convex surface of the condyle inferiorly depressed from the fossa and eminence. This gives surgical access for osteoplasty of the fossa/eminence. The condyle and associated tissue can also be protected from rotary instruments. The retractor is flexible and can be bent to an L shape as shown in FIGS. 17C and 17D.

Figure 18A:
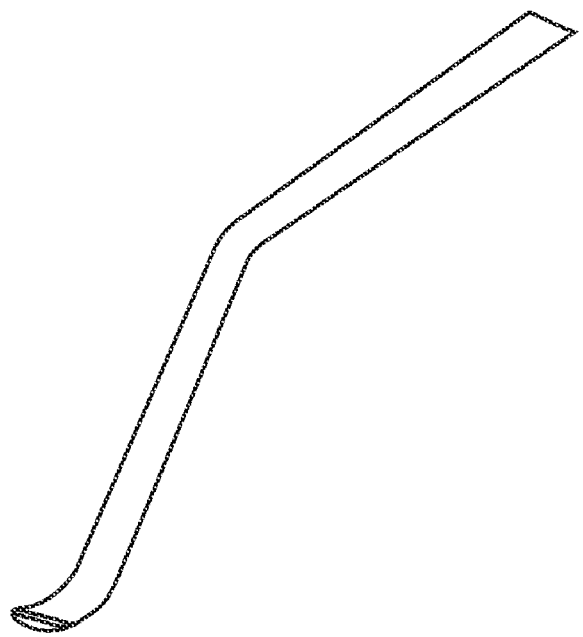
FIGS. 18A and 18B are isometric and side views, respectively, of a third retractor in accordance with another embodiment of the invention that can be used to surgically implant the prosthesis shown in FIG. 2.
Figure 18B:
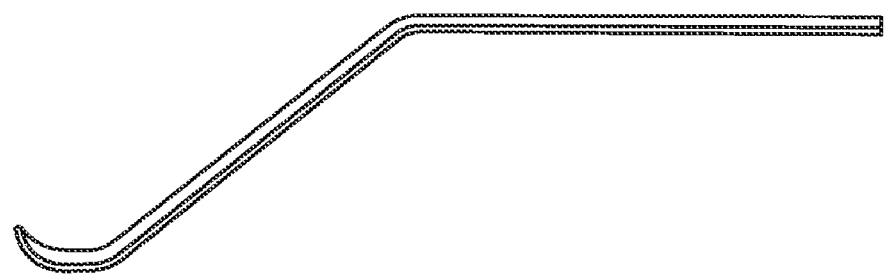

The retractor shown in FIGS. 18A and 18B is a modified channel retractor that can be used for isolating the condyle. The working end is scoop shaped with rounded square angles. The working edge engages the condylar neck inferiorly and isolates the condyle medial pole superiorly. This rotates the mandible laterally allowing access to the medial portion of the mandibular condyle for reshaping.

FIGS. 19A and 19B and 20A and 20B are illustrations of a scraper that can be used for clearing osseous debris present on the fossa and condyle. It is a modified molt curette, and has a concave oblong round scoop working end. The working edges are thin, slightly curved, and sharp. The scraper can also be used for elevating the periosteum at all depths of bone exposure.

Figure 21:
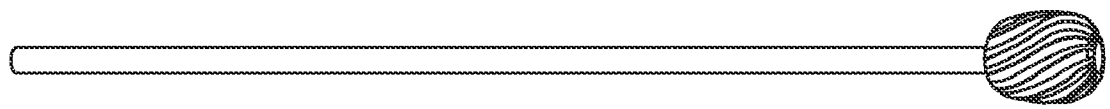
FIG. 21 is a side view of a first burr in accordance with one embodiment of the invention that can be used to surgically implant the prosthesis shown in FIG. 2.
Figure 22:
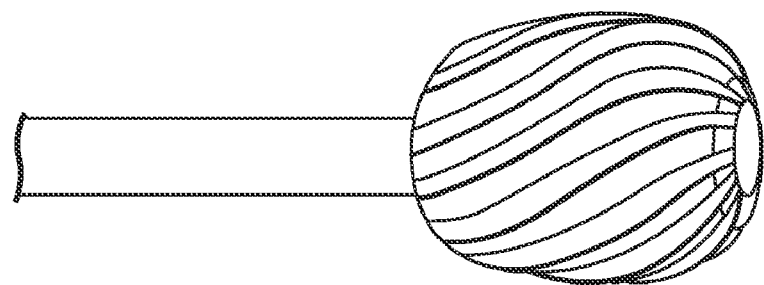
FIG. 22 is a detailed side view of the working end of the burr shown in FIG. 21.

The burr shown in FIGS. 21 and 22 can be used for emino-fossa plasty. The burr is generally pear shaped and configured for cutting both on the end and the side. The cutting edge and angle make it self-cleaning as it reshapes (osteoplasty) the articular eminence and all dimensions of the articular fossa. The burr can also be used to reshape the condyle.

Figure 23:
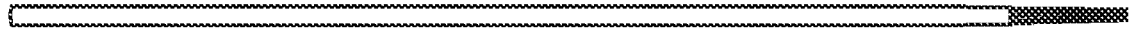
FIG. 23 is a side view of a second burr in accordance with another embodiment of the invention that can be used to surgically implant the prosthesis shown in FIG. 2.
Figure 24:
FIG. 24 is a detailed side view of the tooling end of the burr shown in FIG. 23.
Figure 25A:
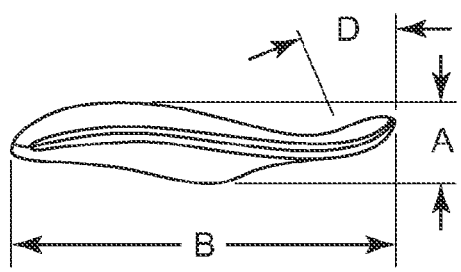
FIGS. 25A-25D are illustrations of a left side prosthesis in accordance with another embodiment of the invention that does not have a posterior projection.
Figure 25D:
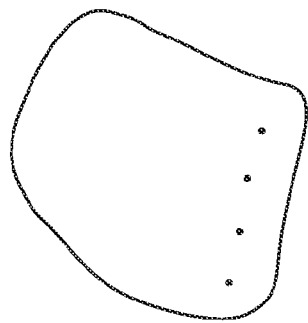
Figure 25B:
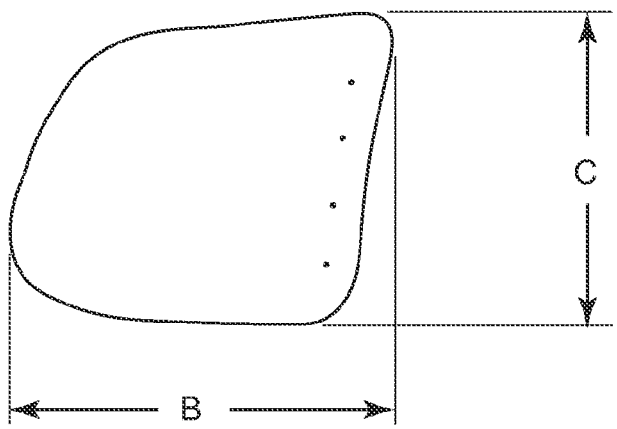
Figure 25C:
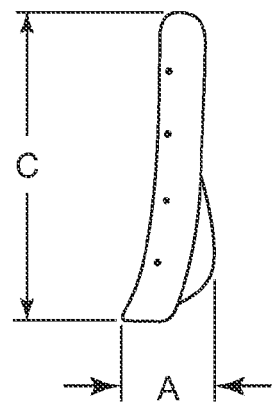

The burr shown in FIGS. 23 and 24 can be used for removing osteophytes and reshaping all dimension of the condyle. It is a self-cleaning side cutting burr.

The embodiments of the prostheses shown in FIGS. 25A-25D are marked to illustrate some example of the dimensions of the devices. Other embodiments of the invention can have other dimensions. Dimension A, the overall height (i.e., in the superior-inferior direction), can, for example, be about 2-10 mm. This is the overall height the prostheses cover in this direction, and is different than the thickness of the prostheses themselves. The thicknesses of the prostheses are not uniform in these embodiments, and can, for example, range from about 1-6 mm. The middle region is typically relatively thicker. Dimension B, the overall width (i.e., in the medial-lateral direction) can, for example, be about 17-33 mm. Dimension C, the overall length (i.e., in the posterior-anterior direction) can, for example, be about 14-30 mm. Dimension D, the angle of the screw holes, can be about 10-30°. Stock prostheses in accordance with the present invention can be distributed in a range of sizes (e.g., with a range of temporal surface areas and a range of thicknesses) suitable for patients having different jaw sizes.

Although the invention has been described with reference to preferred embodiments, those skilled in the art will recognize that changes can be made in form and detail without departing from the spirit and scope of the invention.

What is claimed is:

1. A fossa-eminence hemi-joint prosthesis configured to be surgically fixed to the articular fossa of a patient and to cooperate with the patient's natural mandibular condyle, the prosthesis having a mid region and a condyle-engaging contoured valley having a base at the mid region and configured for engagement with the patient's natural mandibular condyle, the contoured valley having a nonanatomic mandibular fossa surface that is relatively flatter than the patient's native mandibular fossa surface, and wherein the prosthesis is thicker at the base of the valley than at a surrounding area so the surface at the base of the valley will be higher than in an anatomic duplicate of the patient when the prosthesis is implanted in the patient.

2. The prosthesis of claim 1 wherein the mid region of the prosthesis is thicker than other parts to provide the relatively flatter condyle-engaging, mandibular fossa surface.

3. A method for implanting the prosthesis of claim 2 including reducing the articular eminence of the patient before implanting the prosthesis.

4. The prosthesis of claim 2 wherein the mandibular fossa surface has a broader temporal surface coverage than in an anatomic duplicate of the patient when the prosthesis is implanted in the patient.

5. The prosthesis of claim 1 and further including fixation screw holes on a lateral side of the prosthesis.

6. The prosthesis of claim 1 wherein the mandibular fossa surface has a broader temporal surface coverage than in an anatomic duplicate of the patient when the prosthesis is implanted in the patient.

* * * * *